(12) United States Patent
Clarembeau

(10) Patent No.: US 6,646,174 B2
(45) Date of Patent: Nov. 11, 2003

(54) CO-OLIGOMERIZATION OF 1-DODECENE AND 1-DECENE

(75) Inventor: Michel Clarembeau, Temploux (BE)

(73) Assignee: BP Corporation North America Inc., Warrenville, IL (US)

(*) Notice: Subject to any disclaimer, the term of this patent is extended or adjusted under 35 U.S.C. 154(b) by 0 days.

(21) Appl. No.: 10/090,194

(22) Filed: Mar. 4, 2002

(65) Prior Publication Data

US 2003/0166986 A1 Sep. 4, 2003

(51) Int. Cl.[7] .................................................. C07C 2/08
(52) U.S. Cl. ........................................ 585/525; 585/521
(58) Field of Search ................................. 585/525, 521

(56) References Cited

U.S. PATENT DOCUMENTS

| | | | |
|---|---|---|---|
| 4,045,507 A | | 8/1977 | Cupples et al. ........ 260/683.15 |
| 4,045,508 A | * | 8/1977 | Cupples et al. ............. 585/511 |
| 4,950,822 A | | 8/1990 | Dileo et al. ................. 585/310 |

\* cited by examiner

*Primary Examiner*—Thuan D. Dang
(74) *Attorney, Agent, or Firm*—James R. Henes

(57) ABSTRACT

A process for the co-oligomerization of 1-dodecene and 1-decene to produce a polyalphaolefin having a kinetic viscosity of 4 to 6 cSt at 100° C., a Noack weight loss of 4 to 9%, a viscosity index of 130 to 145, and a pour point of −60° C. to −50° C.

9 Claims, No Drawings

CO-OLIGOMERIZATION OF 1-DODECENE AND 1-DECENE

BACKGROUND OF THE INVENTION

1. Field of the Invention

The present invention relates generally to the co-oligomerization of 1-dodecene and 1-decene and more particularly concerns the production of a polyalphaolefin having a kinetic viscosity at 100° C. in the range of from about 4 to about 6 cSt, a Noack weight loss in the range of from about 4 to about 9%, a viscosity index in the range of from about 130 to about 145, and a pour point in the range of from about −60° C. to about −50° C.

2. Discussion of the Prior Arts

Oligomers of alpha olefins and their use as synthetic lubricants are well known. A large market exists for synthetic lubricants that have a viscosity in the range of from 4 to 6 cSt. A low Noack weight loss, a high viscosity index and a low pour point are also desired properties. The use of a hydrogenated oligomer as a synthetic lubricant depends to a large extent on the viscosity of the hydrogenated oligomer. Isoparaffinic oils with kinetic viscosities at 100° C. in the range of from 4 to 6 cSt that are used as synthetic lubricant base stocks, are typically made by oligomerization of 1-decene using a $BF_3$ catalyst and an alcohol promoter. The range of properties for these polyalphaolefins generally include a kinematic viscosity in the range of 4 to 6 cSt at 100° C., a Noack weight loss in the range of about 6 to 15%, a viscosity index in the range of 120–135, and a pour point of less than −55° C.

It is possible to prepare a polyalphaolefin with a kinematic viscosity at 100° C. of 5 cSt with a better viscosity index and Noack weight loss by using 1-dodecene instead of 1-decene as the raw material for such base stocks. When 1-dodecene is used as the raw material, the isoparaffinic oil so prepared typically has a Noack weight loss of 5.5% to 7% and a viscosity index of 143 but a pour point of only −45° C. to about −50° C. Another drawback to the use of 1-dodecene as the raw material is that it does not permit the product of isoparaffinic oils having viscosity below 5 cSt without an unacceptably high Noack weight loss. For instance, an isoparaffinic oil having a 4.5 cSt kinematic viscosity could be prepared by blending a 5 cSt oil made from 1-dodecene with a 4 cSt oil made from 1-decene, but the blend would have a Noack weight loss of 10–11%. Furthermore, using pure 1-dodecene as the raw material in a typical synthesis generally affords large amounts of heavier co-product besides the desired 4–6 cSt material. For example, typically about 70% of a 7 cSt isoparaffinic oil is produced in addition to the desired 5 cSt isoparaffinic oil.

Consequently, it is highly desirable to be able to prepare an isoparaffinic oil base stock having a kinematic viscosity of 4 to 6 cSt at 100° C. and a Noack weight loss in the range of about 4 to about 9%, a viscosity index in the range of from about 130 to about 145 and a pour point in the range of −60° to −50° C. It is also highly desirable to reduce the amount of the aforesaid heavier co-products.

One possible approach may be to use mixtures of 1-olefins as the raw material. DiLeo et al., U.S. Pat. No. 4,950,822 discloses in column 2 lines 63–66 that optimally mixtures of alpha-olefins such as 1-octene, 1-decene and 1-dodecene can be used to arrive at an isoparaffinic oil product having a viscosity suitable for use in an internal combination engine, but does not elaborate further or illustrate that point. Cupples et al., U.S. Pat. Nos. 4,045,507 and 4,045,508 discloses oligomerization processes that are useful with mixtures of 1-olefins as the feed, particularly mixtures of 1-decene with up to about 50 mole percent of 1-octene and/or 1-dodecene.

Thus far no one has disclosed an oligomerization process employing 1-dodecene as a co-monomer for producing an isoparaffinic oil base stock having a kinematic viscosity in the range of from 4 to 6 at 100° C., a Noack weight loss in the range of from about 4 to about 9%, a viscosity index in the range of from about 130 to about 145, and a pour point in the range of from about −60° to about −50° C.

OBJECTS OF THE INVENTION

It is therefore a general object of the present invention to provide an improved ligomerization process employing 1-dodecene and 1-decene as a co-monomer that overcomes the aforesaid problems and meets the aforesaid objectives.

More particularly, it is an object of the present invention to provide an improved aforesaid oligomerization process that produces a product having a kinematic viscosity of from about 4 to about 6 at 100° C., a Noack weight loss of from about 4% to about 9%, a viscosity index of from about 130 to about 145, and a pour point in the range of from about −60° to about −50° C.

It is another object of the present invention to provide an improved aforesaid process that minimizes the amount of heavier byproduct that is produced in addition to the aforesaid product having a kinematic viscosity in the range of from about 4 to about 6.

Other objects and advantages will become apparent upon reading the following detailed description and appended claims.

SUMMARY OF THE INVENTION

These objects are achieved by the process of the present invention for the production of a polyalphaolefin product, comprising co-oligomerizing a mixture comprising from about 60 to about 90 weight percent of 1-dodecene and from about 10 to about 40 weight percent of 1-decene in the presence of a $BF_3$ catalyst and an alcohol promoter at a temperature in the range of from about 20° C. to about 60° C. to thereby form a polyalphaolefin having a kinematic viscosity at 100° C. in the range of from about 4 to about 6 cSt, a Noack weight loss in the range of from about 4 to about 9%, a viscosity index in the range of from about 130 to about 145 and a pour point in the range of from about −60° C. to about −50 ° C.

DETAILED DESCRIPTION OF THE INVENTION

The feedstock for the method of the present invention is a mixture of 1-dodecene and 1-decene. The feedstock is comprised of from about 60% to about 90%, preferably to about 70%, by weight of 1-dodecene and from about 10% to about 40%, preferably to about 30%, by weight of 1-decene.

Preferably, 1-decene is added portionwise during the conduct of the oligomerization. Preferably at least 50%, and more preferably at least 90% by weight of the total amount of the 1-decene employed in the oligomerization is introduced into the reaction mixture containing 1-dodecene and the pressurized atmosphere of boron trifluoride as the oligomerization reaction proceeds. The balance, if any, of the 1-decene is charged to the reactor before commencing the oligomerization reaction. The portionwise feed can be effected by feeding portions of the total 1-decene charge as a series of individual increments over a period of time. In this case the 1-decene is introduced to the reaction mixture as a discontinuous series of small additions until the predetermined amount to be employed pursuant to this invention has been introduced into the oligomerization mixture. Alternatively, and preferably, the feed of 1-decene to the oligomerization mixture is conducted slowly and continuously until the total predetermined amount of the 1-decene has been added. In either case the 1-decene feed rate should be from about 400 parts, preferably from about 600 parts, to about 800 parts by weight of 1-decene per 1000 parts by weight of 1-dodecene and 1-decene per hour.

The boron trifluoride atmosphere within the reactor is typically maintained at a gauge pressure within the range of 1 to 4 bars including 0.05 to 1.5 bars of nitrogen. A preferred pressure range is from 2 to 3 bars gauge with 1 bar (gauge) of nitrogen. Reaction temperatures used in the process are normally in the range of from 20° C. to 60° C. and preferably 35° C. Alcohol promoters that can be used include alkanols having up to about 18 carbon atoms, and preferably up to about 12 carbon atoms, such as, for example, ethanol, 1-propanol, 1-butanol, 2-methylpropanol, 1-pentanol, 1-hexanol, 1-octanol, 2-ethyl-1-hexanol and 1-decanol. Most preferably, the alcohol employed has up to 6 carbon atoms. The most preferred alcohol is 1-butanol. Diols and other polyols can also be used, but are less preferred. One alcohol or a mixture of alcohols can be used as the alcohol promoter. The most preferred mixture of alcohol promoters is a mixture of ethanol and 1-butanol. Preferably more 1-butanol than ethanol is employed, and most preferably a 3:1 weight ratio of 1-butanol to ethanol is employed. The total amount of alcohol promoter employed varies from about 3 to 7 parts per 1000 parts by weight of 1-dodecene and 1-decene with most preferably about 5 parts of alcohol promoter per 1000 parts by weight of 1-dodecene and 1-decene.

Preferably the alcohol catalyst promoter is introduced into the reaction system on a portionwise basis. Preferably at least 50%, more preferably at least 70%, and most preferably at least 90% by weight of the total amount of the alcohol promoter employed is introduced into the reaction mixture as the oligomerization reaction proceeds. The balance, if any, of the alcohol promoter is introduced to the reaction mixture before commencing the oligomerization reaction. The portionwise addition of the alcohol promoter can be effected by feeding portions of the total alcohol charge as a series of individual increments over a period of time. In this case the alcohol promoter is introduced to the reaction mixture as a discontinuous series of small additions until the predetermined amount to be employed pursuant to this invention has been introduced into the oligomerization mixture. Alternatively, and preferably, the feed of alcohol promoter to the oligomerization mixture is conducted slowly and continuously until the total predetermined amount of the alcohol has been added. In either ease the alcohol feed rates should be from 0.8 to 4 parts by weight of alcohol per 1000 parts by weight of 1-dodecene and 1-decene per hour, preferably from 1 to 3 parts of alcohol promoter per 1000 parts by weight of 1-dodecene and 1-decene per hour, and most preferably from 2 to 3 parts of alcohol promoter per 1000 parts by weight of 1-dodecene and 1-decene per hour.

The reaction time needed to effect more than 95% monomer conversion depends on the total amount of alcohol promoter used and on the ratio of 1-decene to 1-dodecene. The higher the relative amount of alcohol promoter is and the more 1-decene employed, the lower the reaction time is. The reaction time for 95% conversion typically varies between 1 and 2 hours.

The following examples will serve to illustrate certain specific embodiments of the invention disclosed herein. These examples are for illustrative purposes only and should not be construed as limiting the scope of the novel invention disclosed herein as there are many alternatives, modifications and variations which will be apparent to those skilled in the art and which fall within the scope and spirit of the disclosed invention.

EXAMPLES 1–14

1-decene employed in the Examples 1–14 had a purity of about 95 mole percent in vinyl olefinic isomer, and 1-dodecene had a purity of about 85 mole percent in vinyl olefinic isomer. The major impurity was vinylidene olefinic isomer and some internal olefins. The oligomerization reactions were performed in a 4522 Parr reactor operated with a conventional laboratory fume hood. The nominal size of the reactor was 2000 milliliters (internal diameter of 4 inches, internal depth of 10.5 inches). The reactor was equipped with a stirring system. When stirring, the axle speed, measured via a tachometer, was set at 200 rpm. There were two six-blade, downward thrust impellers on the stirrer shaft located at 1 and 4 inches from the reactor bottom.

The reactor temperature was regulated at 35° C. with a Parr 4842 controller. The reactor was heated with an electrical mantle that served also as a support. The reaction mixture was cooled with a spiral coil through which cold water was circulated. Opening of the cooling water inlet valve was controlled by the 4842 controller. The reaction temperature was measured with a thermocouple inserted in a thermowell extending to a point near the bottom of the reactor.

Prior to reaction, 1-dodecene was added into the reactor and then the reactor was purged with nitrogen, at 35° C., for 2 hours. The reactor was then pressurized under 2.5 bar $BF_3$. A mixture of the 1-decene and a 1-butanol/ethanol alcohol promoter feed was introduced by means of a Prominent G/4-W membrane pump at flow rate such that the addition was completed in about 30 minutes. 1-decene had been dried under nitrogen before being mixed with the alcohol promoter. The 1-decene feed container was kept under slight nitrogen pressure. $BF_3$ (Air Product, code 2,5: assay 99.5% min.) was added from a 3.6 kilogram bottle connected with a safety regulator fitted with a check valve. The $BF_3$ inlet valve was kept open during the reaction with the pressure regulator set to maintain a 2.5 bar pressure during the whole reaction time. Samples of the crude reaction product were withdrawn through a dip tube in a sampling bottle containing caustic soda.

Distillation was done with a six-tray Oldershaw type distillation column under vacuum. Distillation cuts were hydrogenated on $Pd/Al_2O_3$ (ESCAT 16 from Engelhard). Properties of the hydrogenated materials were measured using CEC method number L40-A-93.

Oligomeric distributions were determined by gas chromatography (stationary phase: Dexil 300 GC). The oligomeric distributions obtained in Examples 1–14 are shown in Table 1.

TABLE 1

| Example No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Reactor heel C12 (g) | 900 | 900 | 900 | 900 | 800 | 800 | 800 | 800 | 700 | 700 | 700 | 700 | 700 | 700 |
| Reactor feed C10 (g) | 100 | 100 | 100 | 100 | 200 | 200 | 200 | 200 | 300 | 300 | 300 | 300 | 300 | 300 |
| EtOH (g) | 1 | 1.3 | 1.3 | 1.8 | 1 | 1.3 | 1.3 | 1.8 | 1.3 | 1.3 | 1.3 | 1.3 | 1.3 | 1.3 |
| BuOH (g) | 2.3 | 2.3 | 4 | 3.3 | 2.3 | 2.3 | 4 | 3.3 | 4 | 4 | 4 | 4 | 4 | 4 |
| Time | 60 | 60 | 60 | 60 | 60 | 60 | 60 | 60 | 60 | 75 | 60 | 60 | 75 | 60 |
| MON. (%) | 52.4 | 49.5 | 30.2 | 2.6 | 15.2 | 23.0 | 10.3 | 9.7 | 1.5 | 1.0 | 2.2 | 2.8 | 5.1 | 0.9 |
| DIM. (%) | 16.9 | 16.3 | 16.2 | 24.2 | 17.7 | 18.0 | 17.9 | 18.5 | 14.2 | 10.7 | 13.3 | 14.0 | 16.5 | 13.7 |
| TRIM. (%) | 22.8 | 26.5 | 35.6 | 55.0 | 49.2 | 44.0 | 55.5 | 50.2 | 57.2 | 52.5 | 55.7 | 57.4 | 54.2 | 56.8 |
| TETRAM. (%) | 7.9 | 7.7 | 10.8 | 15.1 | 15.2 | 12.9 | 15.7 | 17.2 | 22.7 | 26.0 | 21.1 | 20.2 | 19.7 | 22.1 |
| PENT. + (%) | — | — | 7.2 | 3.1 | 2.6 | 2.1 | 0.2 | 4.4 | 4.4 | 9.8 | 7.7 | 5.6 | 4.5 | 6.5 |
| Time | 120 | 120 | 120 | 120 | 120 | 120 | 120 | 120 | 120 | | | | | |
| MON (%) | 1.8 | 2.1 | 1.4 | 1.1 | 1.4 | 1.4 | 1.4 | 1.1 | 1.6 | — | — | — | — | — |
| DIM. (%) | 20.2 | 23.4 | 16.7 | 12.5 | 14.0 | 16.0 | 12.4 | 11.7 | 8.7 | — | — | — | — | — |
| TRIM. (%) | 47.5 | 56.2 | 56.7 | 57.2 | 59.9 | 60.5 | 60.2 | 57.3 | 57.1 | — | — | — | — | — |
| TETRAM. (%) | 20.7 | 13.4 | 19.0 | 23.2 | 21.4 | 20.2 | 22.7 | 22.9 | 25.9 | — | — | — | — | — |
| PENT. + (%) | 9.8 | 4.9 | 6.2 | 6.0 | 3.3 | 1.8 | 3.3 | 7.0 | 6.7 | — | — | — | — | — |

Product of Example 7

The reaction crude obtained after 120 min. of reaction during Example 7 was washed and then distilled to remove lights. After being hydrogenated, the trimer+ product had the properties given in Table 2.

TABLE 2

| Characteristic | Product of Example 7 |
|---|---|
| KV 100° C. (cSt) | 6.1 |
| KV 40° C. (cSt) | 31.94 |
| KV −40° C. (cSt) | 9574 |
| VI | 141 |
| Pour Point (° C.) | −44 |
| Noack (%) | 4.7 |
| % <Trimer | 1.6 |
| % Trimer | 70.1 |
| % Tetramer | 21.1 |
| % Pentamer | 7.2 |

Product of Example 9

The crude reaction product obtained after 120 min. of reaction during Example 9 was washed and then distilled to remove lights. After being hydrogenated, the trimer+ product had the properties given in Table 3.

TABLE 3

| Characteristic | Product of Example 9 |
|---|---|
| KV 100° C. (cSt) | 6.25 |
| KV 40° C. (cSt) | 33.16 |
| KV −40° C. (cSt) | 8610 |
| VI | 141 |
| Pour Point (° C.) | −44 |
| Noack (%) | 4.4 |
| % <Trimer | 0 |
| % Trimer | 58.8 |
| % Tetramer | 30.9 |
| % Pentamer | 10.3 |

Product of Example 10

The crude reaction product obtained after 75 minutes of reaction during Example 10 was washed and then distilled to remove lights. After being hydrogenated, the trimer+ product had the properties given in Table 4.

TABLE 4

| Characteristic | Product of Example 10 |
|---|---|
| KV 100° C. (cSt) | 5.81 |
| KV 40° C. (cSt) | 29.8 |
| KV −40° C. (cSt) | 5110 |
| VI | 142 |
| Pour Point (° C.) | −49 |
| Noack (%) | 4.8 |
| % <Trimer | 1.1 |
| % Trimer | 55.7 |
| % Tetramer | 31.8 |
| % Pentamer | 11.4 |

Products of Example 11 and 12

The crude reaction products obtained after 60 minutes of reaction during Examples 11 and 12 were mixed, and then the mixture was washed. The washed mixture of crude reaction products was distilled to remove lights and recover some trimer (632 grams collected from 1816 grams of reaction crude). After being hydrogenated, the trimer from the distillation overhead (Product A) and trimer+ product from the distillation bottoms (Product B) had the properties given in Table 5.

TABLE 5

| Characteristic | Product A Trimer (dist. overhead) | Product B Trimer + (dist. bottoms) |
|---|---|---|
| KV 100° C. (cSt) | 4.36 | 7.02 |
| KV 40° C. (cSt) | 19.82 | 38.06 |
| KV −40° C. (cSt) | 3068 | 11330 |
| VI | 132 | 144 |
| Pour Point (° C.) | −58 | −49 |
| Noack (%) | 9.1 | 3.0 |
| % <Trimer | 1.3 | 0 |
| % Trimer | 98.7 | 37.9 |
| % Tetramer | 0 | 48.5 |
| % Pentamer | 0 | 13.6 |

Products A and B were blended in a 61.24/38.76 weight ratio to obtain Product C whose properties are shown in Table 6.

TABLE 6

| Characteristic | Product C |
|---|---|
| KV 100° C. (cSt) | 5.21 |
| KV 40° C. (cSt) | 25.27 |
| KV −40° C. (cSt) | 4920 |
| VI | 142 |
| Pour Point (° C.) | −52 |
| Noack (%) | 7.1 |
| % <Trimer | 0.9 |
| % Trimer | 75.1 |
| % Tetramer | 18.7 |
| % Pentamer | 5.3 |

Products of Example 13 and 14

The crude reaction products obtained from Examples 13 and 14 were mixed, and then the mixture was washed. The washed mixture of crude reaction products was distilled to remove lights and recover most of the trimer (703 grams collected from 1448 grams of reaction crude) as distillation overhead (Product D). After being hydrogenated, the trimer (Product D) and product from the distillation bottoms (420 grams) (Product E), had properties given in Table 7.

TABLE 7

| Characteristic | Product D | Product E |
|---|---|---|
| KV 100° C. (cSt) | 4.54 | 8.62 |
| KV 40° C. (cSt) | 20.76 | 52.83 |
| KV −40° C. (cSt) | 3636 | 23270 |
| VI | 136 | 140 |
| Pour Point (° C.) | −50 | −48 |
| Noack (%) | 8.4 | 2.9 |
| % <Trimer | 0.8 | — |
| % Trimer | 99.2 | 6.0 |
| % Tetramer | 0 | 81.6 |
| % Pentamer | 0 | 12.4 |

In Table 8 is presented a comparison of the properties of Product D with those of equiviscous materials (kinetic viscosity at 100° C.) made by blending DS164 either with DS166 or 5cSt made from 100% of 1-dodecene derived polyalphaolefin. DS164 and DS166 was commercially available from BP Amoco Chemical, and the 5 cSt material made from 100% of 1-dodecene was made by BP Amoco Chemical.

TABLE 8

| Characteristic | Product D | DS164/DS166 | DS164/5cSt (100% C12) |
|---|---|---|---|
| KV 100° C. (cSt) | 4.54 | 4.54 | 4.56 |
| KV 40° C. (cSt) | 20.76 | 21.25 | 21.07 |
| KV −40° C. (cSt) | 3636 | 3860 | 3596 |
| VI | 136 | 130 | 135 |
| Pour Point (° C.) | −50 | −60 | −54 |
| Noack (%) | 8.4 | 11.9 | 9.8 |
| Flash Point (PMCC) | 208 | 220 | 218 |
| CCS −30 (cP) | 1170 | 1190 | 1100 |
| CCS −35 (cP) | 1880 | 2010 | 1990 |

11.74 wt % of Product D was blended with 88.26 wt % of Product E in order to obtain a material (Product F) having a similar kinetic viscosity at 100° C. as standard 8cSt materials SHF-83 from Exxon-Mobil and DS168 from BP Amoco Chemical. A comparison of the properties of Product E with those of equiviscous materials (kinetic viscosity of 100° C.) SHF-83 and DS168 presented in Table 9.

TABLE 9

| Characteristic | Product E | SHF-83 | DS168 |
|---|---|---|---|
| KV 100° C. (cSt) | 7.93 | 7.94 | 7.93 |
| KV 40° C. (cSt) | 46.80 | 47.32 | 47.51 |
| KV −40° C. (cSt) | 17979 | 18650 | 18170 |
| VI | 140 | 139 | 137 |
| Pour Point (° C.) | −48 | −50 | −55 |
| Noack (%) | 3.3 | 3.8 | 3.6 |

While the invention is described in connection with the specific examples, it is to be understood that these are for illustrative purposes only. Many alternatives, modifications are variations will be apparent to those skilled in the art in the light of the below examples and such alternatives, modifications and variations fall within the scope and spirit of the appended claims.

What is claimed is:

1. A process for producing a polyalphaolefin product, comprising co-oligomerizing a mixture comprising from about 60 to about 90 weight percent of 1-dodecene and 1-decene in the presence of a $BF_3$ catalyst and an alcohol promoter at a temperature in the range of from about 20° C. to about 60° C. thereby form a polyalphaolefin having a kinematic viscosity at 100° C. in the range of from about 4 to about 6 cSt, a Noack weight loss in the range of from about 4 to about 9%, a viscosity index in the range of from about 130 to about 145 and a pour point in the range of from about −60° to about −50° C., wherein the weight ratio of 1-dodecene to 1-decene is at least about 2:1 and 1-decene is introduced continuously or intermittently during the reaction period.

2. The process of claim 1 wherein at 50% by weight of the total amount of 1-decene employed in the oligomerization is introduced as the oligomerization proceeds.

3. The process of claim 2 wherein the 1-decene feed rate is from about 400 to about 800 parts of 1-decene per 1000 parts by weight by 1-dodecene and 1-decene per hour.

4. The process of claim 1 wherein the alcohol promoter is a primary alcohol.

5. The process of claim 4 wherein the alcohol promoter is at least one of 1-butanol and ethanol.

6. The process of claim 1 wherein the alcohol promoter is employed at a level of from about 0.3 to about 0.7 weight percent of the total weight of 1-dodecene and 1-decene.

7. The process of claim 1 wherein the alcohol promoter is introduced continuously or intermittently as the oligomerization proceeds.

8. The process of claim 1 wherein at least 50% by weight of the total amount of alcohol promoter employed in the oligomerization is introduced as the oligomerization proceeds.

9. The process of claim 8 wherein the alcohol promoter feed rate is from about 0.8 to about 4 parts of alcohol promoter per 1000 parts by weight of 1-dodecene and 1-decene per hour.

* * * * *